United States Patent
Muller et al.

(10) Patent No.: US 10,271,943 B2
(45) Date of Patent: Apr. 30, 2019

(54) METHOD OF FASTENING A SOFT TISSUE GRAFT IN AN OPENING PROVIDED IN A HUMAN OR ANIMAL BONE AND FASTENER SUITABLE FOR THE METHOD

(75) Inventors: Andrea Muller, Winterthur (CH); Andreas Wenger, Muri b. Bern (CH); Jorg Mayer, Niederlenz (CH)

(73) Assignee: SPORTWELDING GMBH, Schlieren (CH)

( * ) Notice: Subject to any disclaimer, the term of this patent is extended or adjusted under 35 U.S.C. 154(b) by 972 days.

(21) Appl. No.: 14/232,640

(22) PCT Filed: Jul. 10, 2012

(86) PCT No.: PCT/CH2012/000158
§ 371 (c)(1),
(2), (4) Date: Apr. 14, 2014

(87) PCT Pub. No.: WO2013/010283
PCT Pub. Date: Jan. 24, 2013

(65) Prior Publication Data
US 2014/0222147 A1 Aug. 7, 2014

Related U.S. Application Data

(60) Provisional application No. 61/508,791, filed on Jul. 18, 2011.

(51) Int. Cl.
*A61F 2/08* (2006.01)
*A61B 17/86* (2006.01)

(52) U.S. Cl.
CPC ........ *A61F 2/0811* (2013.01); *A61B 17/8645* (2013.01); *A61B 17/866* (2013.01);
(Continued)

(58) Field of Classification Search
CPC .................. A61F 2/0811; A61F 2002/0858
See application file for complete search history.

(56) References Cited

U.S. PATENT DOCUMENTS 5,062,843 A * 11/1991 Mahony, III ....... A61B 17/8625
606/232
5,454,811 A 10/1995 Huebner
(Continued)

FOREIGN PATENT DOCUMENTS

CN 1688263 10/2005
EP 2452631 5/2012
(Continued)

*Primary Examiner* — Bruce E Snow
*Assistant Examiner* — Melissa A Hoban
(74) *Attorney, Agent, or Firm* — Rankin, Hill & Clark LLP

(57) ABSTRACT

A soft tissue graft suitable for replacing a tendon or ligament is fastened in a bone opening provided in a human or animal patient by press-fitting an end portion of the graft and a fastener into the bone opening such that the graft end portion is pressed against a first portion of the bone wall inside the bone opening. The fastener is anchored in a second portion of the bone wall by liquefying a material having thermoplastic properties by the fastener and making the fastener penetrate into the bone wall. An end portion of the graft is tied to the fastener with the aid of at least one suture extending from the graft end portion. Tying is carried out after anchoring, during anchoring or between anchoring and press-fitting. The tied connection between the fastener and the graft end portion successfully counteracts potential graft slipping.

11 Claims, 8 Drawing Sheets

(52) U.S. Cl.
CPC .......... *A61F 2002/0817* (2013.01); *A61F 2002/0823* (2013.01); *A61F 2002/0835* (2013.01); *A61F 2002/0858* (2013.01)

(56) References Cited

U.S. PATENT DOCUMENTS

| | | | |
|---|---|---|---|
| 5,632,748 A * | 5/1997 | Beck, Jr. | A61F 2/0811 606/232 |
| 5,871,504 A | 2/1999 | Eaton et al. | |
| 6,099,530 A | 8/2000 | Simonian et al. | |
| 6,264,694 B1 * | 7/2001 | Weiler | A61F 2/0811 623/13.14 |
| 6,328,758 B1 | 12/2001 | Tornier et al. | |
| 6,746,483 B1 * | 6/2004 | Bojarski | A61B 17/0401 623/13.14 |
| 7,335,205 B2 * | 2/2008 | Aeschlimann | A61B 17/00491 433/173 |
| 7,708,761 B2 | 5/2010 | Petersen | |
| 2001/0018619 A1 * | 8/2001 | Enzerink | A61F 2/08 623/23.72 |
| 2002/0165611 A1 * | 11/2002 | Enzerink | A61F 2/1664 623/6.12 |
| 2004/0038180 A1 | 2/2004 | Mayer et al. | |
| 2008/0046091 A1 | 2/2008 | Weiss et al. | |
| 2008/0228186 A1 * | 9/2008 | Gall | A61B 17/0401 606/63 |
| 2009/0222090 A1 | 9/2009 | Mayr et al. | |
| 2010/0023057 A1 | 1/2010 | Aeschlimann et al. | |
| 2012/0053691 A1 | 3/2012 | Hays et al. | |
| 2012/0165868 A1 | 6/2012 | Burkhart et al. | |
| 2012/0265299 A1 | 10/2012 | Beck, Jr. et al. | |
| 2012/0283791 A1 | 11/2012 | Biedermann et al. | |
| 2012/0283830 A1 | 11/2012 | Myers | |
| 2013/0006278 A1 * | 1/2013 | Mayer | A61B 17/686 606/151 |
| 2013/0006302 A1 | 1/2013 | Paulk et al. | |
| 2013/0030479 A1 | 1/2013 | Regauer | |
| 2013/0079875 A1 | 3/2013 | Piccirillo | |
| 2013/0103100 A1 | 4/2013 | Ruffieux | |
| 2013/0138123 A1 | 5/2013 | Stone et al. | |
| 2013/0144334 A1 | 6/2013 | Bouduban et al. | |
| 2013/0144384 A1 | 6/2013 | Gall et al. | |
| 2013/0150885 A1 | 6/2013 | Dreyfuss | |
| 2013/0172998 A1 | 7/2013 | Whittaker | |
| 2013/0184819 A1 | 7/2013 | Donnelly et al. | |

FOREIGN PATENT DOCUMENTS

| | | |
|---|---|---|
| EP | 2452633 | 5/2012 |
| EP | 2596764 | 5/2013 |
| FR | 2924596 | 6/2009 |
| JP | 2005-13740 | 1/2005 |
| JP | 2011-15973 | 1/2011 |
| JP | 2011015973 | 1/2011 |
| WO | 92/04874 | 4/1992 |
| WO | 97/29706 | 8/1997 |
| WO | 2006/023661 | 3/2006 |
| WO | 2010/117982 | 10/2010 |
| WO | 2011/091545 | 8/2011 |
| WO | 2012/068172 | 5/2012 |
| WO | 2012/177386 | 12/2012 |

* cited by examiner

METHOD OF FASTENING A SOFT TISSUE GRAFT IN AN OPENING PROVIDED IN A HUMAN OR ANIMAL BONE AND FASTENER SUITABLE FOR THE METHOD

BACKGROUND OF THE INVENTION

Field of the Invention

The invention generally relates to the field of orthopedic surgery and concerns a method of fastening a soft tissue graft in an opening provided in a human or animal bone, wherein the soft tissue graft comprises an end portion to which a suture is attached or which is suitable for such attachment.

Description of Related Art

The term "soft tissue graft" or just "graft" as used in the present text is in particular an autograft, allograft or xenograft, but it may also be an original soft tissue to be re-attached to a bone from which it has been detached by injury or surgery. The soft tissue graft is in particular a tendon or ligament graft or an original tendon or ligament. However, the term "soft tissue graft" or "graft" is meant to encompass also prosthetic elements replacing or complementing soft tissue, i.e. in particular artificial tendon or ligament tissue or tendon or ligament substitutes or partial substitutes that are to replace or strengthen a ruptured or otherwise defective tendon or ligament and, for such purpose, are to be fastened in a bone opening. It could also encompass the extension of a meniscus graft or textile ribbons which are known as alternatives to cerclage wires, wires, or plate/screw systems, for example for fixing bone fragments, or for stabilizing fractures or osteotomies.

The term "bone" as used in the present text is a piece of a viable bone tissue, which may be complemented with artificial bone replacement material.

The term "suture" as used in the present text is a suture as used in surgery but may also be another suitably flexible lengthy fixation element such as, for example, a ribbon, cable or wire.

At least one end portion of the soft tissue graft has at least one suture attached thereto or is suitable for such attachment. This means that the suture is attached to the soft tissue graft either by a manufacturer or by the operating team, wherein in the latter case such attachment is carried out either ex situ (in the operating room) or in situ (in the operation site). In addition to its function according to the invention, which will be detailed below, the suture will usually have further per se known functions such as, for example, re-enforcing the soft tissue graft, combining a plurality of graft strands, adapting a cross section of an end portion of the graft to a cross section of the bone opening or a fastener, in situ positioning and/or tensioning the graft and so on. The attachment of the suture to the soft tissue graft may, for example, be achieved by stitching (in particular per se known stitched graft ends) or by threading the suture through a folded end of the graft or through an eyelet-like feature provided on the end of the graft. If the soft tissue graft itself is suture-like, i.e., is a suitably flexible fine ribbon or cable, the graft itself may serve as the named suture being attached to the graft in the widest sense of the term "attached".

The opening provided in the bone for the fastening according to the invention is in a per se known manner a tunnel leading through the bone or a blind opening extending into the bone from a bone surface and comprising a closed end within the bone. This opening is preferably provided by drilling but can also be provided by, for example, punching (ultrasonic punching), i.e. this opening will often have a circular or non-circular cross section remaining the same over most of the depth of the opening, but this is not a condition for the invention. The opening may also have a plurality of sections with differing cross sections, may have a conical form, or may be undercut (for example made by milling that allows production of three dimensional geometries within the opening).

One exemplary application of the method and fastener according to the invention (the same as for known such methods and fasteners) is the replacement of a ruptured anterior cruciate ligament (ACL) in a human knee with a graft that is fastened, on the one hand, in an opening extending from the articular surface of the distal femur end and, on the other hand, in an opening extending from the tibia plateau, for example in a femoral blind opening and a tibial tunnel, wherein the tibial tunnel has a second mouth in the outer surface of the tibia below the tibia plateau. Therein the ruptured anterior cruciate ligament is usually replaced by a graft, such as, for example, a patellar tendon graft comprising two terminal bone blocks, a hamstring tendon graft (semitendinosus tendon, possibly combined with gracilis tendon), usually being folded and stitched in the end region, i.e. not comprising terminal bone blocks, or a quadriceps tendon graft, which is usually harvested with one terminal bone block. The named grafts are usually autografts but may also be donor grafts (allografts). Donor grafts may also be made of achilles tendons. It is further proposed to use synthetic ribbons and suitably treated tendon material of slaughtered animals (xenografts), such as pigs. The named autografts and allografts may furthermore be reinforced with synthetic material.

Further application fields of the method and fastener according to the invention are, for example, surgical procedures regarding the human foot or ankle, such as lateral ankle reconstruction, FDL tendon transfer (flexor digitorum longus), FHL tendon transfer (flexor hallucius longus), or flexor to tendon transfer (second toe); surgical procedures regarding the human hand such as ligament reconstruction tendon interposition, scapholunate ligament reconstruction, collateral ligament reconstruction, or UCL repair (ulnar collateral ligament) of the thumb (also known as "gamekeeper's thumb"); surgical procedures regarding the human elbow such as UCL repair (ulnar collateral ligament), or distal biceps tendon repair; or surgical procedures regarding the human shoulder such as proximal biceps tendon repair. A further example is the repair of torn or damaged cranial cruciate ligaments (CCL) in stifle joints in particular of dogs but also of other animals, such as cats. The CCL is the most commonly damaged stifle ligament in dogs and the named repair is carried out using nylon bands that are passed around the fabella bone in the back of the femur and are fixed in a bore provided in the front part of the tibia.

DESCRIPTION OF RELATED ART

According to known ACL-surgery procedures, end portions of the above named grafts are fastened in the above named openings in femur and tibia with the aid of interference screws, which are screwed into the opening when the graft is positioned therein, or with the aid of non-threaded, mechanically expandable or non-expandable press-fit elements, which may comprise retention means such as barbs and are forced into the opening without rotation when the graft is positioned therein or together with the graft. Various devices and methods for such fixation are described e.g. in the publications U.S. Pat. Nos. 5,454,811 and 6,099,530

(both to Smith & Nephew), EP-0317406 (Laboureau), US-2009/222090 (Mayr) or WO 2006/023661 (Scandious Biomedical).

It is further known from the publication WO 2011/091545 to fasten ends of soft tissue grafts in bone openings with the aid of non-threaded press-fit elements wherein the press-fit element is forced into the opening to clamp the graft against a first portion of the wall of the opening and is then anchored in a second portion of the wall of the opening with the aid of a liquefiable material, preferably a material having thermoplastic properties, and mechanical vibration (or other suitable energy). Therein the liquefiable material is comprised by an anchoring element to be combined with the press-fit element or it is integrated in the press-fit element. It is liquefied in situ by application of the mechanical vibration to the anchoring element or the press-fit element and is made to penetrate in the liquid state into the trabecular structure or into specifically provided cavities of the bone tissue of the wall of the opening, where, on re-solidification, it forms a positive fit connection between the press-fit element and the bone tissue. This anchorage reinforces the press-fit connection between the bone tissue and the press-fit element which is prone to loosening through relaxation of the bone tissue. According to the above referenced publication WO 2011/091545, the step of press-fitting and the step of anchoring are carried out after each other and independent from each other.

Most of the above named known methods for fastening a soft tissue graft in a bone opening provide satisfactory retention of the fastener in the bone opening but show potential weaknesses regarding the retention of the graft either due to damage of the graft through retention means (e.g. screw thread) provided on the fastener or due to graft slipping in a time period shortly after the surgery when there is not yet enough tissue growth in the bone opening for integrating the graft and therewith enhancing its retention in the opening. Graft slippage is a potential weakness in particular in graft fastening methods that rely primarily on a press-fit and for implantation in bone tissue of non-optimal quality (for example, bone tissue of elderly patients), wherein experiments show that providing retention means on the graft side of the fastener is hardly able to improve the situation, necessitating in many cases additional external fixation. Prevention of graft slipping is, of course, an important issue in particular if the fastened soft tissue graft is to remain tensioned and/or if its eventual length is critical, which is in particular the case for tendon and ligament grafts. It is furthermore important in cases for which, due to the anatomic situation or due to the surgical technique, it is desired to keep the press-fit strength to a minimum.

For preventing graft slipping some authors propose to secure an ACL graft, in addition to fixation in a bone tunnel or instead of the latter, at least on the tibial side but possibly also on the femoral side by fixing sutures extending from the graft end (or the graft itself) on the bone surface in the region of the one tunnel mouth which is not situated in the articular surface using, for example, a bone screw or a similar fixation device. However, such known additional external fixation techniques, in particular a washer/screw fixation on the front side of the tibia, tends to cause problems because of the little coverage by soft tissue if they cannot be removed as soon as possible after the main operation.

SUMMARY OF THE INVENTION

It is an object of the invention to create a further method and fastener for fastening a soft tissue graft in an opening provided in a bone of a human or animal patient, wherein the method and fastener improve upon known methods and fasteners serving the same purpose, regarding graft slipping. The method and fastener according to the invention are particularly suitable for soft tissue grafts that need to be fastened in a bone opening while being tensioned, but are also applicable when this is not the case.

The present invention is a further development of the method and fastener disclosed in the above referenced publication WO 2011/091545, the entire disclosure of which is enclosed herein by reference. This means that, the same as disclosed in the referenced publication, also according to the invention, the soft tissue graft is fastened in the bone opening with the aid of a press-fit fastener, wherein the fastener, when press-fitted in the bone opening and clamping the graft against a first portion of the wall of the opening is anchored in a second portion of the wall of the opening with the aid of a material having thermoplastic properties, which is liquefied in situ and made to penetrate into the wall of the opening where, on re-solidification, forms a positive-fit connection between the fastener and the wall of the opening. The fastener includes a press-fit element and an anchoring element, wherein the anchoring element comprises the material having thermoplastic properties and is either separate from the press-fit element or integrated therein. After these per se known method steps, according to the invention, the soft tissue graft is tied to the anchored press-fit fastener with the aid of the at least one suture attached to the end portion of graft (or possibly, for a suture-like graft of a sufficient length, with the aid of an end piece of the graft itself) thereby indirectly connecting the graft to the anchorage of the fastener and therewith providing an insurance against graft slippage.

Preferred materials having thermoplastic properties used for the anchoring step have an initial modulus of elasticity of at least 0.5 GPa and a melting temperature of up to about 350° C. They are bio-degradable, such as, for example, polylactides (e.g. LR706PLDLLA 70/30, R208 PLDLA 50/50, L210S or PLLA100% all by Böhringer) or non-degradable such as, for example, Polycarbonateurethane (e.g Bionate by DSM). Further examples of suitable materials having thermoplastic properties and of filler materials are disclosed in the publication WO 2011/091545, page 13, line 17 to page 16, line 2. The preferred energy used for liquefaction of the material having thermoplastic properties is mechanical vibration energy, in particular ultrasonic vibration energy having a frequency in the range of 2 to 200 kHz (preferably between 15 and 30 kHz).

The method according to the invention comprises basically the following three steps:
  press-fitting an end portion of the soft tissue graft in the bone opening with the aid of a fastener,
  anchoring the fastener in the wall of the bone opening with the aid of in-situ liquefaction of a material having thermoplastic properties,
  tying the end portion of the graft to the fastener with the aid of at least one suture extending from this end portion.

Therein the step of anchoring is necessarily carried out after the step of press-fitting, and the step of tying is preferably carried out after the step of anchoring, but may also be carried out simultaneously with the step of anchoring, between the steps of press-fitting and anchoring, or even before the step of press-fitting.

Depending on the required graft tension and on the strength of the graft retention provided by press-fitting, it is advantageous to keep the graft tensioned by external means not only during the press-fitting step and the anchoring step but also during the tying step. Depending on the manner in which the suture is tied to the fastener it may be advantageous to provide sutures (or other means) for external graft tensioning which are separate from the sutures provided for the tying. If graft tension is maintained during all the method steps by external means or if graft tension is not a major requirement to be achieved by the surgery, the strength of the press-fitting achieved in the press-fitting step may be only little, which means that the major part of the graft and fastener retention in the bone opening is provided by the anchorage of the fastener in the bone wall on the one hand and by the tying of the graft to the fastener on the other hand. This also means that the fastening according to the invention needs to rely on the press-fitting much less than known methods using press-fit fasteners and is therefore possible and successful also in bone tissue in which strong press-fitting is not possible or in which press-fitting relaxes fast such that it cannot retain the graft satisfactorily until graft integration by new tissue growth is able to fully take over such retention. Furthermore, the fastening method according to the invention makes it possible to adapt the press-fit strength to specific operation sites, surgical techniques etc., without regard to graft slipping.

The step of tying the graft to the fastener and the corresponding equipment of the fastener depend in particular on the chosen step sequence, on the type of fastener, on the number of sutures attached or attachable to the graft and on the direction of potential graft slipping. Preferred embodiments of the method according to the invention are applicable using per se known stitched graft end portions, which comprise a plurality of suture ends extending from the very end of the graft. In further embodiments the sutures used for the tying to the fastener extend not from the very graft end but at a small distance therefrom.

For enabling the tying, the fastener (press-fit element or anchoring element) and/or a suitable suture retainer used in addition to the fastener preferably comprises at least one suture passage through which at least one suture used for the tying is threaded and relative to which the suture is locked. If only one suture is available for the tying or if an available plurality of sutures is threaded together through one only suture passage, preferably a suture retainer is used for locking the suture(s) in the passage, or the passage is collapsed or the suture(s) extending from the suture passage is stitched to graft near the exit of the suture passage. If a plurality of sutures are available for the tying, these may be threaded in opposite directions through one suture passage or through different suture passages and/or along surface portions of the fastener and are then fastened together by being knotted together and/or with the aid of a suitable suture retainer.

Threading of the suture(s) through the suture passage(s) may constitute a preliminary step for the tying step, wherein this preliminary step may be carried out ex-situ (before the press-fitting step) or in situ (before or after the anchoring step) and wherein the fastener (press-fit element or anchoring element) and/or the suture retainer is slid along the suture(s) threaded therethrough before the tying is finalized.

The steps of press-fitting and of anchoring and fasteners equipped for these steps are per se known from the further above referenced publication WO 2011/091545, wherein as above mentioned the fastener comprises a press-fit element and an anchoring element, the latter being a separate element or being integrated in the press-fit element. According to the disclosure of the referenced publication, the press-fit connection is achieved using a fastener dimensioned for being forced into the opening (corresponding dimensioning of fastener and opening) or using a fastener that is positioned in the opening and is then expanded, wherein forcing or positioning the fastener in the opening is carried out either when the soft tissue graft is already positioned in the opening or together therewith and wherein forcing or positioning without rotation of the fastener is preferred but not a necessity. The soft tissue graft to be fastened is arranged in the opening such that it does not cover the whole wall of the opening and the fastener is oriented such that a fastener portion equipped for achieving the anchoring is facing a wall portion not covered by the soft tissue graft. The anchoring element is positioned relative to the press-fit element before the step of press-fitting (anchoring element integrated in press-fit element) or after the step of press-fitting (separate anchoring element) and, in the anchoring step, the anchoring element is advanced relative to the press-fit element using an anchoring tool that simultaneously transmits the energy needed for the in situ liquefaction to the anchoring element.

As, for example, disclosed in the publications WO2010/045751 and WO2009/141252 (Nexilis), it is possible also to firstly treat the bone wall of the opening with a first portion of liquefiable material such that the trabecular structure of this wall is penetrated and therewith re-enforced by the liquefiable material and only then press-fitting fastener and graft in the opening and carrying out the above described anchoring step, wherein a second portion of liquefiable material is welded to the pretreated wall of the opening. This two step anchoring procedure results in a same positive-fit connection as the above described single step procedure if the first and second portions of liquefiable material comprise the same liquefiable material. However, the first and second portions may comprise different liquefiable materials under the condition that the two materials are weldable to each other under the conditions of the anchoring step.

For achieving a good anchorage it may be advantageous or even necessary to provide, in addition to or in place of pores or cavities of the trabecular network of the bone tissue, further cavities in the bone wall of the opening to be filled with the liquefied material (e.g. undercut form of opening in the bone tissue).

For the separate fastener functions of pressing the soft-tissue graft against the bone wall of the bone opening and of anchoring (positive-fit connection with bone tissue of the wall of the opening), the fastener according to the invention comprises separate surface portions equipped either for the pressing function or for the anchoring function. The surface portions equipped for the pressing function may, in a per se known manner, have a flat or concave form (shallow groove) and be rough or otherwise structured for retention of the soft tissue graft to be fastened, but may also lack any specific form or structure. The surface portions equipped for the anchoring function are formed to be positioned in close proximity to the wall of the bone opening and include means for guiding the liquefiable material from the fastener inside or from the proximal fastener face to these surface portions or include the liquefiable material. Furthermore, the latter surface portions may include reaming or cutting edges, threads, barbs or other per se known structures for additional support of the fastener in the bone wall of the opening.

In a preferred fastener embodiment the surface portions equipped for either pressing or anchoring constitute sectors of a circumferential surface, wherein a fastener suitable for fastening a one-strand graft or a multi-strand graft with an end portion in which the strands are not separated (extra-graft fastening), one pressing sector and one anchoring sector, and wherein a fastener suitable for fastening a two-strand or multi-strand graft with an end portion in which the strands or groups thereof are separated (intra-graft fixation) comprises a plurality of such sector pairs. Alternatively, the fastener surface portions equipped for either pressing or anchoring may be arranged beside each other along a fastener axis, or such alternatively arranged surface portions may be provided on the fastener in addition to the above named surface sectors.

The fastener has, for example, the general form of a cylinder, frustum or cone (continually tapering or stepped), preferably but not necessarily with substantially circular cross sections, i.e. is suitable for being fitted into an opening of a substantially circular cross section (cylindrical or tapering continually or in steps), but it may also have another form such as a parallelepiped or wedge.

Instead of using vibrational energy for creating the local thermal energy needed for the liquefaction of the material having thermoplastic properties, it is possible also to exploit other energy types, in particular, as disclosed in WO2010/127462 rotational energy turned into friction heat in substantially the same manner as the vibrational energy, or electromagnetic radiation (in particular laser light in the visible or infrared frequency range), which radiation is preferably guided through the material having thermoplastic properties and locally absorbed by an absorber being contained in the material having thermoplastic properties or being arranged adjacent to this material. Electric energy (resistive heating) can also be used.

BRIEF DESCRIPTION OF THE DRAWINGS

Exemplary embodiments of the method and the fastener according to the invention are described in detail in connection with the appended drawings, wherein.

Items having the same function and similar items are denominated in all Figs. with the same reference numerals.

DESCRIPTION OF PREFERRED EMBODIMENTS

Figure 1:
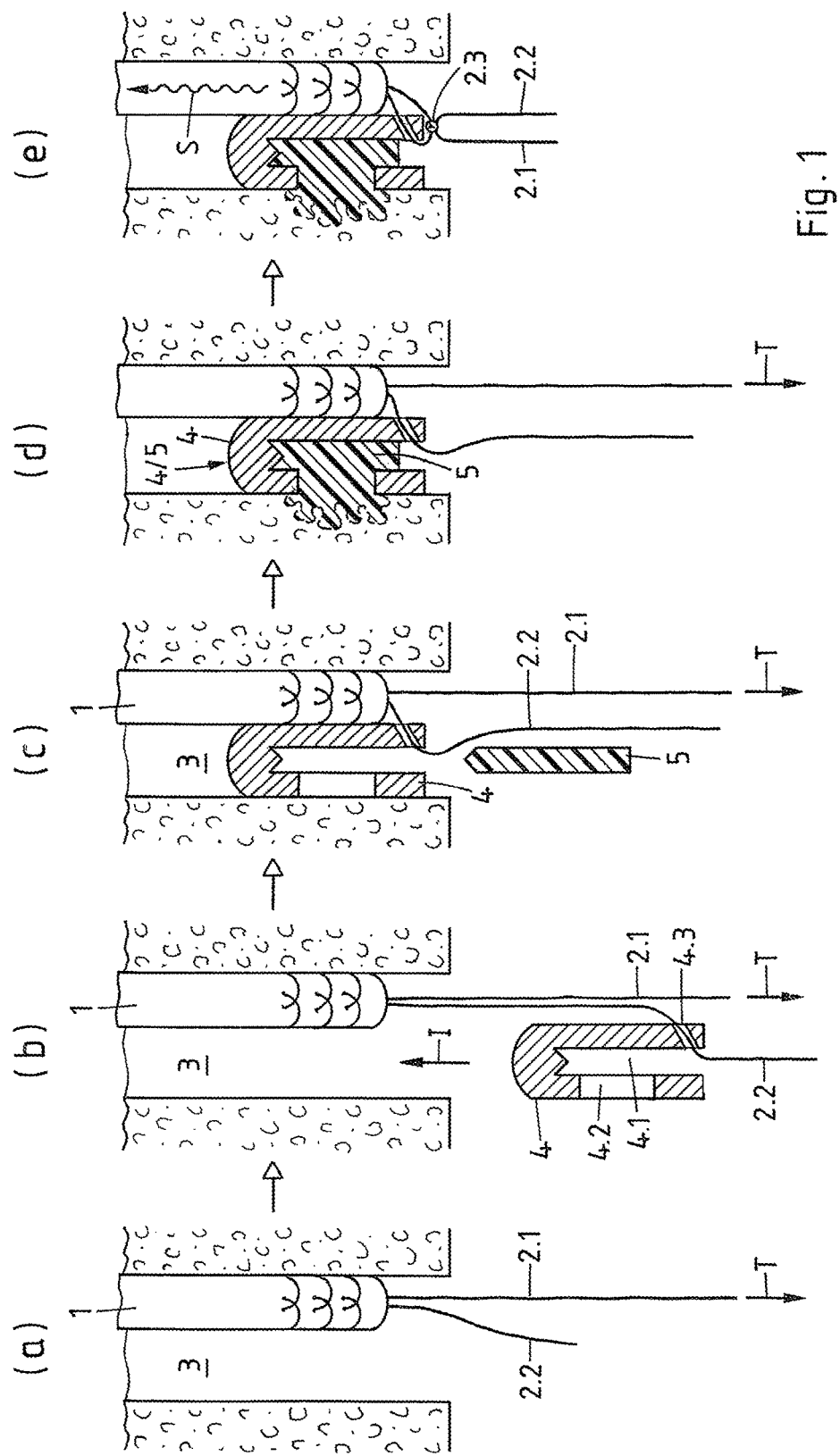
FIG. 1 shows five consecutive phases (a) to (e) of an exemplary embodiment of the method according to the invention for fastening a soft tissue graft in a bone tunnel with the aid of a first exemplary embodiment of the fastener according to the invention, wherein graft slippage to be counteracted by the graft being tied to the fastener has a direction which is substantially the same as the direction in which the fastener is introduced into the bone tunnel.

FIG. 1 illustrates a first exemplary embodiment of the method and the fastener according to the invention and shows the progress of the method in five consecutive phases (a) to (e), wherein the end portion of the graft, the fastener and the bone tunnel in which the graft is to be fastened are shown axially sectioned. The fastener 4/5 comprises a press-fit element 4 and a separate anchoring element 5. The bone tunnel, of which only the one mouth through, which the fastener is introduced, is shown, is, for example, a tibial tunnel provided for fastening a second end portion of an ACL-graft whose first end portion is already fastened in a femoral blind opening or tunnel, wherein the fastener is introduced into the tibial tunnel through the tunnel mouth not situated in the tibia plateau. During at least part of the method steps, the graft is tensioned (if applicable) by being pulled in a direction T opposite to the direction I in which the fastener is introduced into the bone tunnel Potential graft slipping (arrow S) to be counteracted by the graft being tied to the fastener has a direction away from the tunnel mouth through which the fastener is introduced, i.e. its direction is substantially the same as the implantation direction I.

Phase (a) shows the end portion of the soft tissue graft 1 with a first and a second suture 2.1 and 2.2 attached thereto such that the sutures extend from the very graft end, as this is usually the case for graft ends which are stitched in a per se known manner. The very end of the graft 1 is to be positioned within the bone tunnel 3, its distance from the tunnel mouth, through which the fastener is introduced, preferably being chosen such that the proximal fastener face does not protrude from the bone tunnel (see further phases). If applicable, the graft is kept tensioned (arrow T) by at least one of the two sutures (first suture 2.1) being connected to an external tensioning means, for example, being pulled away from the bone by a member of the operating team.

Phase (b) shows the press-fit element 4 of the fastener, which is preferably substantially cylindrical (preferably but not necessarily having a substantially circular cross section) and is equipped for fastening the graft end portion in the tunnel 3 by press-fitting, anchoring and tying. For the anchoring the press-fit element 4 comprises a cavity 4.1 that is open at a proximal face of the press-fit element and that is connected by a fenestration 4.2 or perforation to the circumferential surface at the one press-fit element side, which is to face the tunnel wall. For the tying step the press-fit element 4 comprises a suture passage 4.3 with a passage entrance on the circumferential press-fit element surface on the one fastener side that is to face towards the graft and an exit in the proximal press-fit element face or in the cavity 4.1. The second suture 2.2 is threaded trough the suture passage 4.3 from its entrance to its exit, i.e. finally extending from the proximal press-fit element face. If the first suture 2.1 is not used for maintaining graft tension, it is possible also to initially thread both sutures through the suture passage and to un-thread the first suture 2.1 for the tying step, wherein for the un-threading a hooked tool may be used. In phase (b) the press-fit element 4 is shown positioned for being introduced into the bone tunnel (implantation direction I).

Phase (c) shows the press-fit element 4 being positioned in the bone tunnel 3 (after the press-fitting step) during which the press-fit element 4 is slid along the second suture 2.2 (or possibly both sutures) towards the tunnel mouth and forced into the tunnel 3 between the graft end portion and the tunnel wall to a depth such that the entrance to the suture passage 4.3 is positioned the same deep as or less deep than the very end of the graft 1 or the location on the graft from which the second suture 2.1 issues from the graft. During the introduction of the press-fit element 4, the graft 1 is kept tensioned, for example, with the aid of the first suture 2.1. The depth to which the press-fit element is introduced into the tunnel is best limited by keeping the second suture 2.2 tight, for example, by holding it together with the first suture 2.1. Phase (c) also shows the separate anchoring element 5 ready for the anchoring step.

Phase (d) shows the fastener 4/5 (press-fit element 4 and the anchoring element 5) and the end portion of the graft 1 after the anchoring step, during which the anchoring element 5 is pressed into the cavity 4.1 of the press-fit element 4 and suitable energy (preferably ultrasonic vibration energy) is applied to the anchoring element 5 causing the material having thermoplastic properties comprised by the anchoring element 5 to be liquefied, to be forced through the fenestration 4.2 or perforation and to penetrate into the tunnel wall, where on re-solidification it firmly anchors the fastener to this tunnel wall. External graft tensioning (arrow T) is preferably maintained during the anchoring step but can be stopped thereafter.

Phase (e) shows the graft end portion after the step of tying, i.e. the completed fastening. In the tying step, the end portion of the graft 1 is tied to the fastener 4/5 or to the anchored press-fitting element 4 respectively by, for example, knotting the first suture 2.1 and the second suture 2.2 together (knot 2.3) in the region of the proximal fastener face. The tying needs to be effected such that the two sutures are both tight enough for being able to counteract slippage (arrow S) of the graft 1 relative to the fastener or the tunnel wall respectively on relaxation of the press-fit, on releasing the external graft tensioning, or on early loading of the graft 1.

As mentioned above, the method as illustrated in FIG. 1 makes it necessary to introduce the fastener 4/5 into the bone tunnel 3 such that the entrance to the suture tunnel 4.3 has a depth that is the same as or smaller than the depth of the very graft end or generally speaking the depth of the graft location from which the suture being threaded through the suture passage 4.3 originates. Furthermore it is advantageous for the fastener 4/5 to be positioned in the tunnel 3 such that neither the proximal fastener face nor the knot 2.3 protrude from the tunnel mouth. This means that in the case of the fastening of an ACL-graft or a similar fastening it is necessary to provide a graft having a length that corresponds within predetermined limits to a predetermined length. Experiments show that it is easily possible to provide ACL-grafts having a length of 90 mm±2.5 mm and that such accuracy regarding the graft length is quite sufficient for carrying out the method according to the invention. Alternatively, the required graft length can be measured intra-operatively using per se known tools, therewith determining the correct graft length prior to graft stitching and placement.

FIG. 1 further shows that for the shown embodiment of method and fastener, the press-fit element 4 needs to have an axial length that is larger by the axial extent of the suture passage 4.3 than a minimal press-fit element length necessary for a satisfactory press-fit. For specific applications this may be a draw-back which, however, can be overcome, for example, by attaching the second suture 2.2 to the graft end portion such that it extends not from the very graft end but from a location distanced from the latter (see embodiment of FIG. 2).

Further exemplary embodiments of method and fastener according to the invention result from the following variations of method and fastener as shown in FIG. 1:

The press-fit achieved in the press-fitting step is strong enough or graft tension is not important and therefore it is possible to stop external tensioning of the graft 1 already between the step of press-fitting and the step of anchoring.

The press-fit achieved in the press-fitting step is not strong enough for maintaining the desired graft tension and therefore it is necessary to maintain external graft tensioning until completion of the tying step, which necessitates further sutures not involved in the tying or a corresponding tensioning tool such as e.g. a hooked rod.

Figure 7:
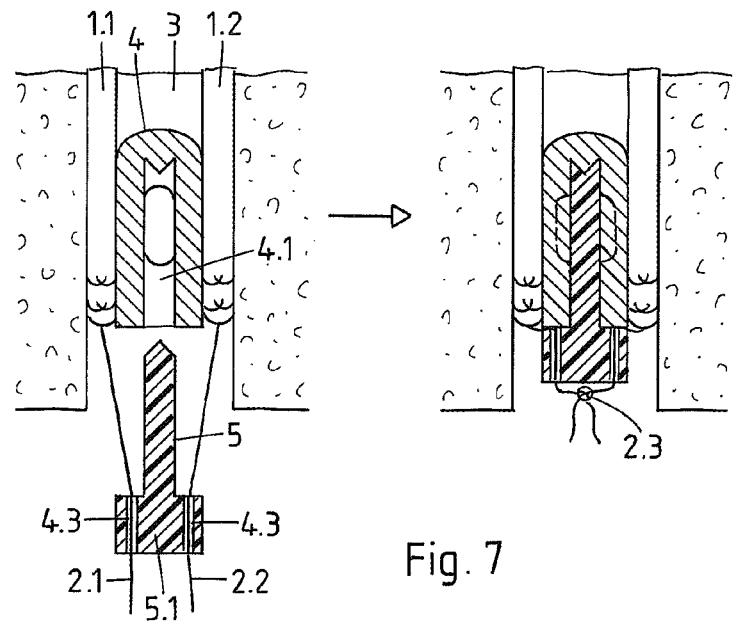
FIGS. 7, 8A/B, 9 illustrate further exemplary embodiments of method and fastener according to the invention, wherein the end portion of the graft comprises two separate strands and wherein at least one suture extends from each one of the graft strands (intra-graft fixation) and wherein graft slippage to be counteracted has a direction as discussed in connection with FIG. 1.

Instead of from a graft end portion being clamped as one unit between the fastener and the wall of the bone opening (extra-graft fixation), the two (or more than two) sutures extend from separated sections of the graft end portion, wherein the different sections are clamped separately between the fastener and the wall of the bone opening (intra-graft fixation) as, for example, shown in FIG. 7).

Instead of tying the graft 1 to the press-fit element 4 by knotting the two sutures 2.1 and 2.2 together, a per se known suture retainer may be used, the suture retainer being deformed or welded to the sutures, for example, using vibratory energy. In the same manner it is possible to weld the two sutures together or to weld them to the fastener, i.e. to the press-fit element 4 or to the anchoring element 5, which means for the latter case that the tying step may be carried out substantially simultaneously with the anchoring step.

Instead of knotting the two sutures 2.1 and 2.2 together, the second suture 2.2 only (or both sutures) is locked in the suture passage 4.3 by fastening a suture retainer to it at the exit of the suture passage 4.3 or on the proximal face of the press-fit element 4 or by collapsing the suture passage 4.3. If both sutures 2.1 and 2.2 extend through the suture passage 4.3 it is possible also to use a button-like suture retainer having at least two through bores and a cross section larger than the exit of the suture passage 4.3 or the cavity 4.1 respectively, to thread the sutures through the retainer and to knot them together beyond the suture retainer.

The press-fit element 4 comprises two suture passages, wherein each one of the two sutures is threaded through one of the passages, graft tension advantageously being maintained with the aid of a further suture or a corresponding tool such as a hooked rod.

The suture passage 4.3 is constituted by an eyelet arranged on the proximal face of the press-fit element (see also FIG. 9), wherein only the second suture 2.2 is threaded through the eyelet or the two sutures 2.1 and 2.2 are threaded through the eyelet in opposite directions and are then knotted together or are locked in the eyelet by a suture retainer or by collapsing the eyelet.

More than two sutures extend from the graft end portion, wherein some of the sutures are not involved in the tying but are, for example, used for keeping the graft under tension and/or wherein the first and/or the second suture are each constituted by a plurality of sutures.

The graft is suture-like and an end piece of the graft represents at least one of the sutures.

As disclosed in the publication WO 2011/091545 (FIG. 14 described p. 33/1.1 to p. 33/1.13), the cavity 4.1 of the press-fit element extends at an angle to the fastener axis having an open mouth both on the proximal face of the press-fit element and on its circumferential surface, the latter constituting the fenestration 4.2 shown in FIG. 1.

As disclosed in the publication WO 2011/091545 (FIG. 5, described p. 27/1.4 to p. 28/1.18), the anchoring element 5 is tube-shaped and held between a counter element and a foot piece of an anchoring tool, which extends through the counter element and the anchoring element, wherein for effecting the anchoring, the foot piece and a distal end of the anchoring element are positioned inside the cavity 4.1. The material having thermoplastic properties comprised by the anchoring element is liquefied by applying vibratory energy through the tool to the foot piece and is made to flow into the cavity 4.1 and through the fenestration 4.2 into the tunnel wall by pushing the foot piece and the counter element against each other.

As disclosed in the publication WO 2011/091545 (FIGS. 6 and 7, described p. 28/1.19 to p. 30/1.18) the press-fit element 4 comprises instead of the cavity 4.1 and the fenestration 4.2 at least one groove extending along its circumferential surface in a substantially axial direction and the anchoring element 5 is forced into this groove being in direct contact with the tunnel wall.

As disclosed in the publication WO 2011/091545, the anchoring element 5 is not a separate fastener part but is integrated in the press-fit element 4, by being situated in the cavity 4.1 already before the step of anchoring.

As disclosed in the publication WO 2011/091545 (FIGS. 8 and 9A/B, described p. 30/1.19 to p. 32/1.2), the anchoring element 5 is integrated in the press-fit element 4, by the press-fit element comprising a corresponding portion of the material having thermoplastic properties or being fully made of this material. For effecting the anchoring an anchoring tool of a suitable cross section is applied to the proximal fastener face either near its circumference or in a central area, wherein in the latter case, the fastener comprises a cavity 4.1 similar to the cavity described in connection with FIG. 1, the cavity having a cross section smaller than the anchoring tool and the material having thermoplastic properties being arranged around this cavity.

Figure 6:
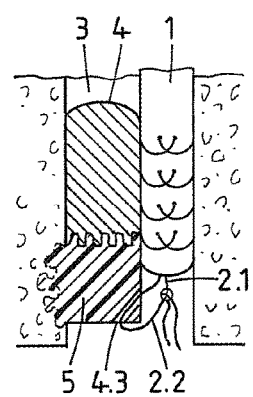

As disclosed in the publication WO 2011/091545 (FIG. 25, described p. 38/1.21 to p. 40.115), the separate anchoring element 5 is anchored in the wall of the bone opening 3 between the mouth of the opening through which the press-fit element 4 is introduced into the opening and the proximal press-fit element face and is at the same time welded to or anchored in the proximal press-fit element face, wherein the suture passage 4.3 is preferably comprised by the anchoring element 5 (see FIG. 6).

As disclosed in the publication WO 2011/091545 (FIG. 23, described p. 36/1.14 to p. 37/1.18), before carrying out the press-fitting step, the wall of the bone tunnel may be re-enforced at least partially through interpenetration of the bone tissue by a second material having thermoplastic properties, wherein in the anchoring step the first material having thermoplastic properties comprised by the anchoring element is welded to the second material present in the tunnel wall.

As disclosed in the publication WO 2011/091545 (FIGS. 37 and 38A/B, described p. 45/1.8 to p. 47/1.23), the fastener or press-fit element is introduced into the bone tunnel by being slid along a K-wire and for this purpose comprises an axial channel which extends centrally or ex-centrically and which may be constituted over part of the axial length by the cavity 4.1.

FIGS. 2 to 6 illustrate further exemplary embodiments of method and fastener according to the invention. The figures are axial sections through the one portion of the bone tunnel 3 in which the end portion of the graft 1 and the fastener are located after completion of the fastening, i.e. after the press-fitting step, the anchoring step, and the tying step. The embodiments shown in FIGS. 2 to 6 are, for example, suitable for the same applications as the embodiment illustrated in FIG. 1 and the method in which the fastening of the soft tissue graft is accomplished is about the same as illustrated in FIG. 1 or as mentioned above as alternatives thereof. The differences between the embodiment as shown in FIG. 1 and the embodiments shown in FIGS. 2 to 6 mainly regard the suture passage(s), the way in which the suture or sutures are threaded through the suture passage(s) and the way in which the suture or sutures extend from the end portion of the graft.

Figure 2:
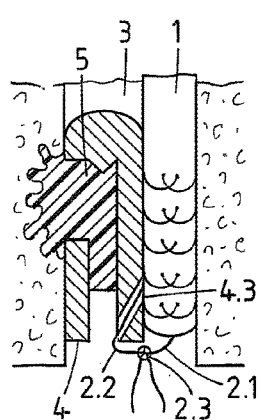
FIGS. 2 to 6 illustrate a plurality of further exemplary embodiments of the fastener applicable in the method according to the invention and in particular in the method as illustrated in FIG. 1.

In the embodiment according to FIG. 2 the second suture 2.2 being threaded through a similar suture passage 4.3 as shown in FIG. 1 does not extend from the very end of the graft 1 but from a location at a distance from this very end, which distance is about the same as or longer than the distance between the entrance to the suture passage 4.3 and the proximal fastener face. This means that the fastener 4/5 can be positioned in the bone tunnel 3 with its proximal face at a depth equal or even greater than the depth of the very end of the graft 1, which eliminates the above mentioned draw-back of the embodiment according to FIG. 1 regarding exploitation of only part of the axial fastener length for the press-fit.

Figure 3:
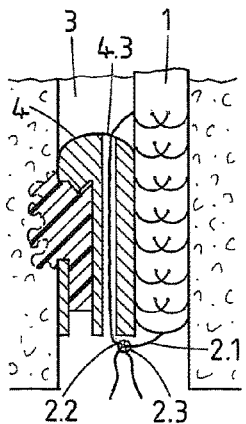

In the embodiment according to FIG. 3, the suture passage 4.3 extends axially through the fastener 4/5 (entrance of passage at the distal fastener end) and the second suture 2.2 extends from the graft end portion at a distance from the very graft end which distance is substantially equal to or greater than the axial length of the fastener 4/5. The suture passage 4.3 may further serve for guiding the press-fit element along a K-wire into the tunnel 3.

Figure 4:
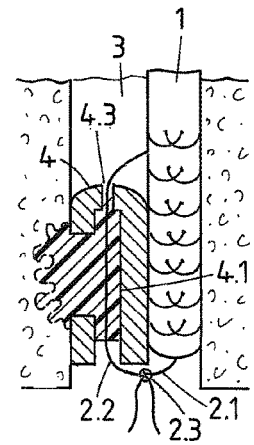

In the embodiment according to FIG. 4, the suture passage 4.3 extends axially through the fastener 4/5 as shown in FIG. 3 but is, for example, partly constituted by the cavity 4.1. Threading and tying of the sutures is similar as above described in connection with FIG. 3. However, it is possible also to lock the second suture 2.2 (or both sutures) in the cavity 4.1 with the aid of the liquefied material of the anchoring element, i.e. during the anchoring step. If such locking constitutes a sufficiently strong tie between the fastener 4/5 and the suture 2.2, knotting together of the two sutures 2.1 and 2.2 or use of a suture retainer may not be necessary.

Figure 5:
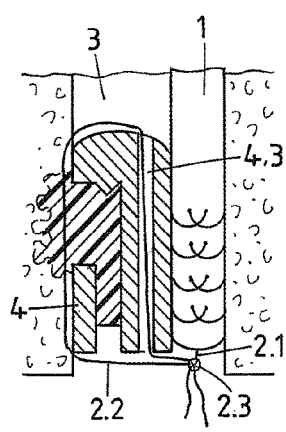

In the embodiment according to FIG. 5 the suture passage 4.3 extends axially through the fastener 4/5, wherein other than shown in FIGS. 3 and 4, the proximal passage mouth is used as its entrance. The two sutures 2.1 and 2.2 extend from the very fastener end, the second suture 2.2 being threaded through the suture passage from its proximal mouth to its distal mouth and along the circumferential fastener surface back to the proximal fastener face, where it is tied to the first suture 2.1. Instead of the knotting together the two sutures or in addition to the knotting (or a suitable suture retainer), the second suture 2.2 may also be locked relative to the fastener 4/5 by the material having thermoplastic properties that may re-solidify around the second suture 2.2. The circumferential fastener surface on the one fastener side facing the tunnel wall may define a groove for accommodation of the second suture 2.2.

In the embodiment according to FIG. 6, the separate anchoring element 5 is anchored in the wall of the bone tunnel 3 in a location between the tunnel mouth through which the press-fit element 4 is introduced and the proximal press-fit element face and the suture passage 4.3 is provided by the anchoring element 5. Simultaneously with being anchored in the tunnel wall, the anchoring element 5 is preferably welded to or anchored in the proximal face of the press-fit element 4. The second suture 2.2 is threaded through the suture passage 4.3 before the anchoring step and the anchoring element 5 is slid along the second suture 2.2 for carrying out the anchoring step. It is possible also to provide the suture passage 4.3 as a groove across the distal face of the anchoring element 5 and possibly from there to the proximal face of the anchoring element, and instead of or in addition to the knotting together of the two sutures (or instead of a suitable suture retainer) to lock the second suture 2.2 in the groove during the anchoring step when the distal face of the anchoring element 5 is attached to the proximal face of the press-fit element and therewith the groove is collapsed.

Figure 8A:
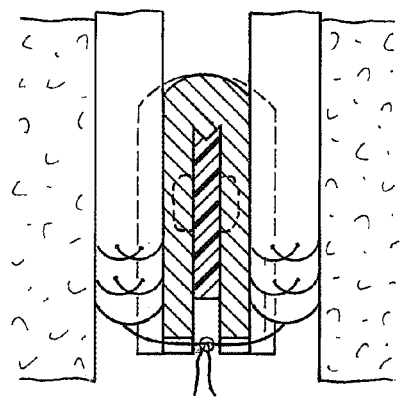

FIGS. 7 and 8A/B illustrate further exemplary embodiments of method and fastener according to the invention, wherein other than illustrated in FIGS. 1 to 6 the graft end portion (or the whole graft) to be fastened with the aid of the fastener comprises two separate graft strands (or separate groups of graft strands), wherein at least one suture extends from each one of the graft strands and wherein the fastener is introduced into the bone opening between the graft strands. The same so called intra-graft fixation is possible for graft end portions comprising more than two separate strands or groups of strands and correspondingly equipped fasteners. All embodiments and variants thereof as described above are applicable also for intra-graft fixation.

FIG. 7 illustrates the above named intra-graft fixation with two axial sections through bone tunnel 3, graft strands 1.1 and 1.2 with sutures 2.1 and 2.2, press-fit element 4 and anchoring element 5 before the anchoring and tying steps (left hand side) and after completion of the fastening (right hand side). The press-fit element 5 comprises two opposite sides equipped for the anchorage (in FIG. 7 facing against and away from the viewer) and, therebetween, two sides equipped for clamping the graft strands against the wall of the bone opening (in FIG. 7 two lateral sides). At least one suture 2.1 and 2.2 extends from each one of the graft strands 1.1. and 1.2. The suture passages 4.3 through which the sutures 2.1 and 2.2 are threaded are provided in the anchoring element 5 as already illustrated in FIG. 6, wherein according to FIG. 7 the anchoring element 5 comprising the material having thermoplastic properties and to be introduced and liquefied in the cavity 4.1 of the press-fit element 4 as already shown in FIGS. 1 to 5, further comprises a proximal appendix 5.1 which has, for example, a larger cross section than the anchoring element 5 and through which, for example, two suture passages 4.3 extend.

The fastener 4/5 according to FIG. 7 is implanted in the same manner as described above for the fasteners according to FIGS. 1 to 6, wherein the sutures 2.1 and 2.2 are threaded through the suture passages 4.3 before the step of anchoring and wherein for the step of anchoring the anchoring element 5 with its proximal appendix 5.1 is slid along the sutures. In the step of tying the two sutures 2.1 and 2.2 are, for example, knotted together, the suture passages are collapsed or a suitable suture retainer is used.

Other than shown in FIG. 7, the proximal appendix 5.1 of the anchoring element 5 may be made of a different (e.g., non-liquefiable) material than the distal part of the anchoring element which serves for the anchoring. Furthermore, the proximal appendix 5.1 may be a separate part (suture retainer) being positioned on the proximal face of the press-fit element 4 or the anchoring element 5 after the step of anchoring wherein the step of tying may comprise deforming this suture retainer by application of vibration energy for collapsing the suture passages and at the same time welding the suture retainer to the anchoring element.

Figure 8B:
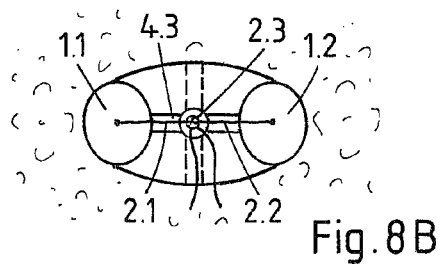

FIGS. 8A and 8B illustrate a further intra-graft fixation according to the invention in axial section (FIG. 8A) and viewed against the tunnel mouth and against the proximal fastener face (FIG. 8B). The fastener 4/5, which is equipped for fastening two grafts or two separate strands 1.1 and 1.2 of one graft, is positioned in a bone tunnel 3, which preferably has a non circular oblong cross section, wherein the fastener 4/5 is positioned between the two graft strands 1.1 and 1.2. Of the two sutures 2.1 and 2.2 one extends from either one of the graft strands 1.1 and 1.2, and in the tying step these sutures are tied together by, for example, being knotted together. Therein two suture passages 4.3 are provided, which may have, for example, the form of grooves in the proximal fastener face. It may even be possible to not provide any suture passages.

Figure 9:
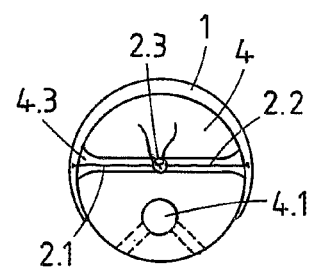

FIG. 9 shows an embodiment which is quite similar to the ones illustrated in FIGS. 7, 8A, and 8B, but wherein the two sutures 2.1 and 2.2 do not extend from two separate graft strands or two separate grafts but from two edge regions of a ribbon-shaped graft 1. The suture passages 4.3 and the tying step are substantially the same as described for the embodiments according to FIG. 7, 8A, or 8B.

Figure 10:
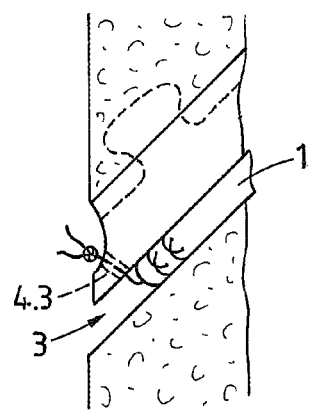
FIG. 10 shows a soft tissue graft fixation according to the invention in a tibial tunnel.

FIG. 10 illustrates an embodiment of the fastener 4/5 according to the invention that is in particular suitable for fastening an end portion of an ACL-graft (graft 1) in a tibial tunnel or for another application in which the axis of the bone tunnel 3 extends at an acute angle from the bone surface through which the fastener is introduced into the tunnel. In such a case it is desired (the same as in other cases) that the fastener does not protrude from the tunnel mouth, that a maximum of the fastener length is effective for the press-fit and that still the fastener or the press-fit element respectively comprises a proximal face which allows safe impaction with as little as possible shear between the impaction tool and the named proximal face, i.e. it is further desired that at least a part of the proximal face of the press-fit element extends substantially perpendicular to the tunnel axis. For best satisfying all the named desires it is proposed to provide the suture passage 4.3 in a fastener portion, which protrudes ex-centrically from the proximal fastener face, wherein portions of the proximal face other than where the protrusion is located are substantially perpendicular to the fastener axis and therefore suitable for being acted on with the impaction tool, and wherein the fastener 4/5 is introduced into the tunnel 3 with the protruding portion facing away from the acute angle.

The variations listed above in connection with FIG. 1 are mostly applicable for the embodiments according to FIGS. 8A, 8B, 9 and 10 also.

Figure 11:
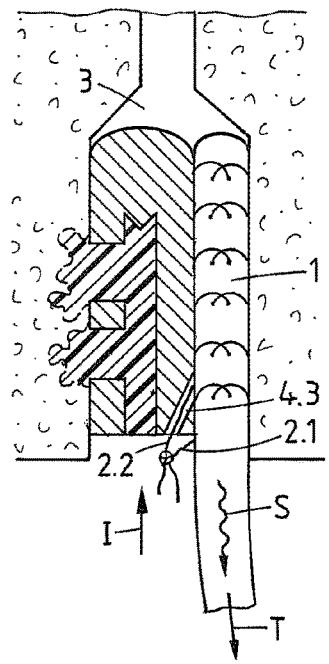
FIGS. 11 to 14 illustrate further exemplary embodiments of method and fastener according to the invention, wherein a soft tissue graft is fastened in a bone tunnel or a blind opening, and wherein graft slippage to be counteracted by the graft being tied to the fastener has a direction which is substantially opposite to the direction in which the fastener is introduced into the bone tunnel or blind opening.
Figure 12:
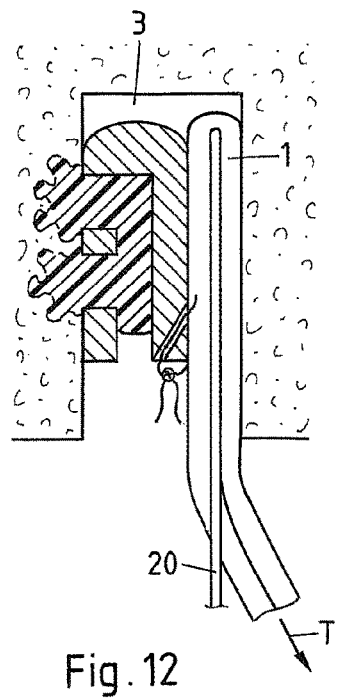

FIGS. 11 to 14 illustrate further exemplary embodiments of method and fastener according to the invention. These embodiments differ from the embodiments as illustrated in FIGS. 1 to 10 by the graft protruding from the mouth of the bone opening through which the fastener is introduced and by the potential graft slipping to be counteracted by tying the graft to the fastener, when the fastener is press-fitted and possibly anchored in the bone opening, having a direction opposite to the direction in which the fastener is introduced into the bone opening. The bone opening may not only be a bone tunnel, possibly with a smaller cross section located away from the tunnel mouth through which the fastener is introduced (FIG. 11), but it may also be a blind opening (FIGS. 12 to 14). This method is, for example, suitable for fastening an ACL-graft in a femoral opening, being either a tunnel or a blind opening.

FIG. 11 shows the end portion of the graft 1 and the fastener 4/5 in the bone tunnel 3, wherein the fastener 4/5 is press-fitted and anchored in the tunnel and wherein the tunnel has a portion with a smaller cross section beyond the distal end of the fastener or distanced from the tunnel mouth through which the fastener is introduced respectively.

For carrying out at least the step of press-fitting, the graft 1 is tensioned by, for example, being fixed in the region of the not shown tunnel mouth (e.g., with the aid of the end of a suture extending from the very end of the graft 1 or with the aid of a corresponding tool) and by being pulled (arrow T) out of the tunnel mouth through which the fastener 4/5 is introduced. For the step of tying the graft 1 to the fastener 4/5, the fastener 4/5 comprises at least one suture passage 4.3, for example as illustrated in FIG. 1, and the graft 1 comprises at least one suture (2.1 and 2.2) extending from the graft end portion at a distance from the very end of the graft. The steps of press-fitting and of anchoring are carried out as above described in connection with the preceding FIGS. 1 to 10 and variants thereof, wherein, however, introduction of the fastener 4/5 into the tunnel 3 is to be effected such that the entrance to the suture passage 4.3 has a depth in the tunnel that is the same or greater than the depth of the location at which the suture 2.2 originates from the graft 1. The step of tying is carried out as above described in connection with FIGS. 1 to 10 and described variants thereof. However, as the graft protrudes from the bone opening 3 further embodiments for the tying step become possible such as, for example, stitching the at least one suture to the graft or tying two sutures around the graft.

FIG. 12 illustrates a further exemplary embodiment of method and fastener according to the invention, wherein the method and the fastener are similar to the ones illustrated in FIG. 11, with the difference that the bone opening 3 is a blind opening and therefore the tension of the graft 1 is maintained by pushing the graft end towards the bottom of the blind opening 3 with the aid of a pushing tool 20 and at the same time pulling an other end of the graft 1 away from the mouth of the opening 3 (arrow T), through which the fastener is introduced into the opening. The end of the graft 1 on which the pushing tool 20 acts is, for example, a folded graft end and the pushing tool 20 is, for example, a rod comprising a forked end.

Obviously, removal of the pushing tool 20 relaxes the press fit achieved in the press-fitting step at least partly. Therefore, at least if graft tension is important, the pushing tool is removed best only when the fastening is finished, i.e. after the tying step.

For the steps of press-fitting and anchoring as well as for the fastener features substantially all the previously described embodiments and variants thereof are applicable also for the embodiment according to FIGS. 10 and 11.

FIGS. 13A to 13G illustrate a further exemplary embodiment of method and fastener according to the invention similar to the embodiments illustrated in FIGS. 11 and 12, wherein however, the at least one suture 2.2 extends from the very end of the graft 1 and the press-fit element 4 comprises an axial suture passage 4.3 through which the suture 2.2 (or sutures) is threaded from its distal mouth to its proximal mouth. This preliminary step of threading needs to be carried out before the step of press-fitting, and the end portion of graft 1 and the press-fit element 4 need to be introduced into the bone opening 3 together, while the suture 2.2 is kept tight and the press-fit element 4 is advanced along the suture to be about flush with the very graft end.

Figure 13A:
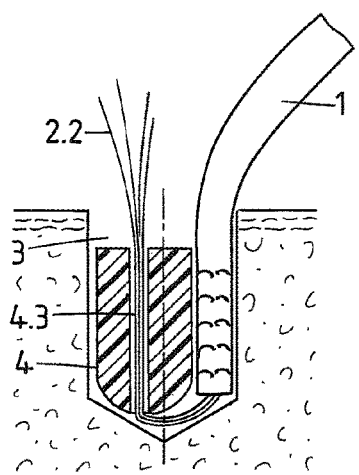
Figure 13B:
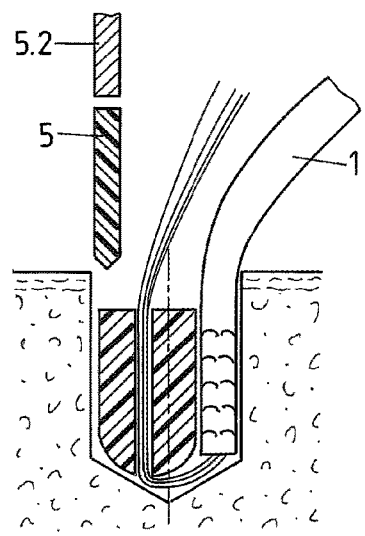
Figure 13C:
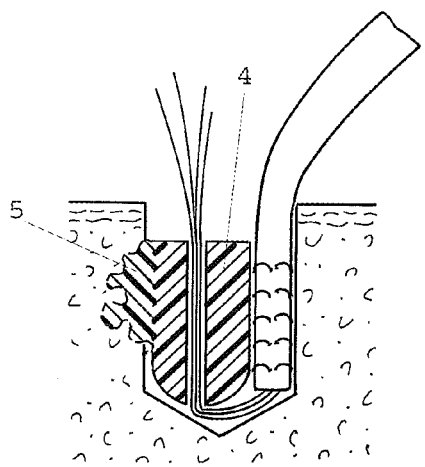
Figure 13D:
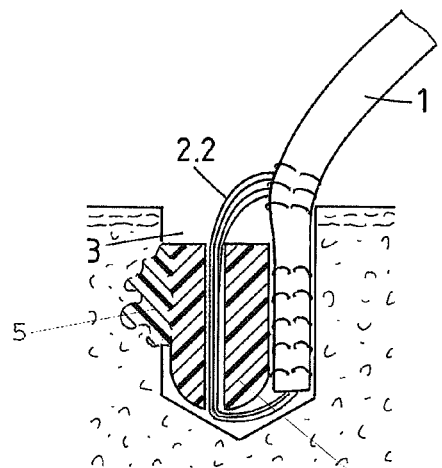

FIG. 13A shows the end portion of the graft 1 and the press-fit element 4 introduced in the bone opening 3; FIG. 13B further shows the anchoring element 5 and an anchoring tool 5.2 ready for the anchoring step; FIG. 13C shows the anchored fastener 4/5; FIG. 13D shows the graft end portion being tied to the fastener, wherein in this embodiment the at least one suture 2.2 is, for example, stitched to the graft end portion in the area where the graft protrudes from the bone opening 3. Alternatively, two sutures may be threaded round the graft on different sides and knotted together or a suture retainer may be used as described further above.

Figure 13E:
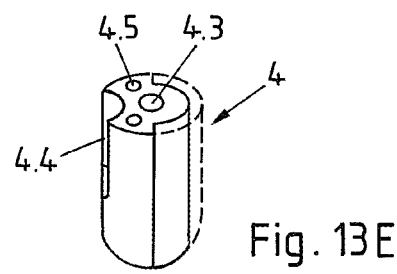
Figure 13F:
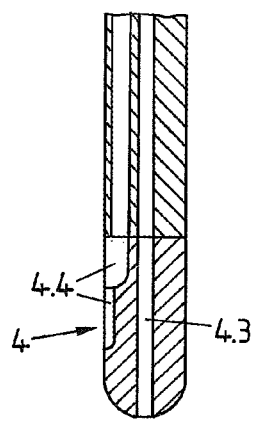
Figure 13G:
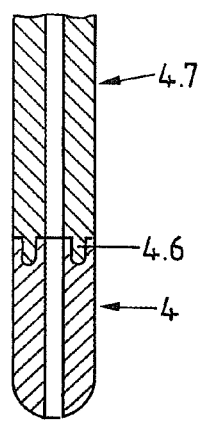

FIGS. 13E to 13G show an exemplary press-fit element 4, which is applicable in the method illustrated in FIGS. 13A to 13G, FIG. 13E being a three dimensional representation of the press-fit element 4 and FIGS. 13F and 13G being perpendicular axial sections through the press-fit element 4 and through an impaction tool 4.7 applicable for introducing the press-fit element 4 and the graft end portion into the bone opening 3. For the anchoring of the fastener in the wall of the blind opening 3, the press-fit element 4, for example, comprises a groove 4.4 extending in axial direction along its circumferential surface and the form of the anchoring element 5 is adapted to the groove. Other fastener equipment for the anchoring (e.g., cavity with fenestration as described in connection with FIG. 1) as described further above is applicable for this embodiment also. The press-fit element 4 further comprises an axial suture passage 4.3 and, in its proximal face, two blind bores 4.5 cooperating with two protrusions 4.6 on the distal face of the impaction tool 4.7, bores and protrusions serving for holding the press-fit element 4 on the distal end of the impaction tool 4.7. Instead of cooperating protrusions and bores for holding the press-fit element on the distal end of the impaction tool, for example, cooperating screw threads, means for a push-on or snap-on connection, means for elastic compression and/or expansion, or clamping means may be provided.

The impaction tool 4.7 further comprises an axial suture channel aligned with the suture passage 4.3 of the press-fit element 4 and a further axial channel aligned with the groove 4.4 provided in the press-fit element 4.

FIGS. 14A to 14F illustrate a further exemplary embodiment of method and fastener according to the invention wherein the method is quite similar to the one illustrated in FIG. 12. Other than in the embodiment according to FIG. 12 it is not the end portion of the graft 1 that is acted on by the pushing tool 20 but the at least one suture 2.2 extending from the very graft end. The pushing tool may, for example, be a K-wire with a split end.

Figure 14A:
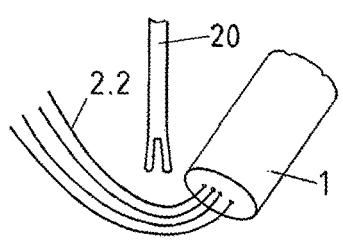
Figure 14B:
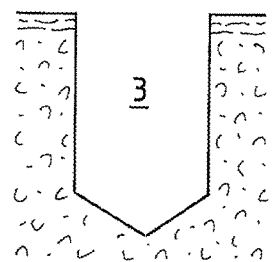
Figure 14B:
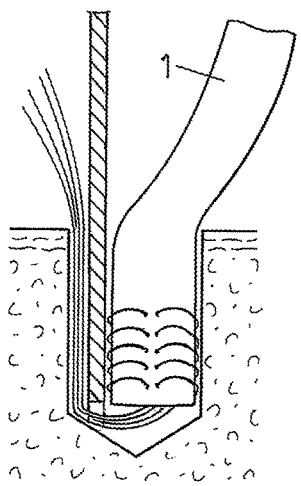
Figure 14C:
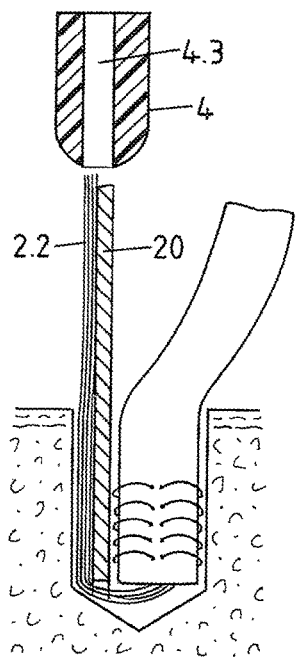
Figure 14D:
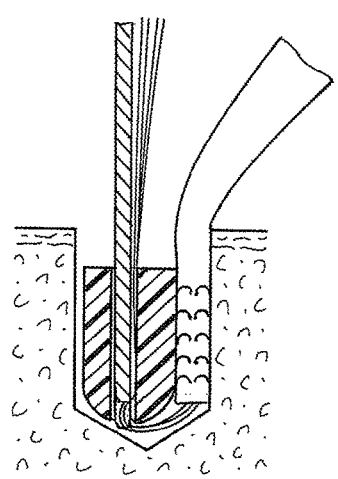
Figure 14E:
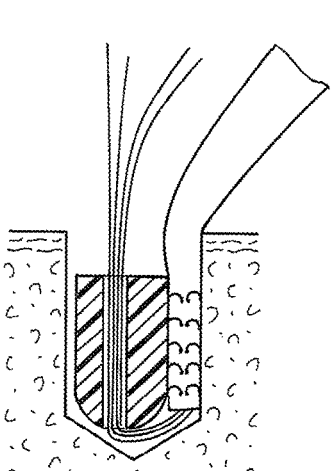
Figure 14F:
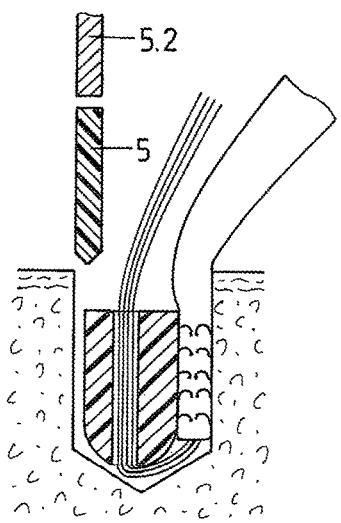

FIG. 14A shows the end portion of the graft 1 and the pushing tool 20 ready for introduction into the bone opening 3 and FIG. 14B shows the graft end portion and the pushing tool 20 introduced in the bone opening 3. FIG. 14C shows the introduction of the press-fit element 4, wherein the pushing tool 20 serves for guiding this introduction, the press-fit element 4 being slid along the pushing tool 20 wherein both the pushing tool 20 and the suture 2.2 extending through the axial suture passage 4.3 of the press-fit element 4. FIG. 14D shows the press-fit element 4 and the graft end portion after the press-fitting step and FIG. 14E the same after removal of the pushing tool 20. FIG. 14F illustrates the start of the anchoring step (anchoring element 5 and anchoring tool 5.2 ready for the anchoring step). The anchoring step and the tying step are carried out as, for example, described above in connection with FIGS. 13B to 13D. An exemplary embodiment of the press-fit element 4 suitable for the method as illustrated in FIGS. 14A to 14F is the one illustrated in FIGS. 13E to 13G.

Embodiments of method and fastener according to the invention as illustrated in FIGS. 11 to 14 are not only applicable for extra-graft fixation as illustrated in FIGS. 11 to 14 but, if adapted according to FIGS. 7 and 8A/B, they are applicable also for intra-graft fixation.

Figure 15:
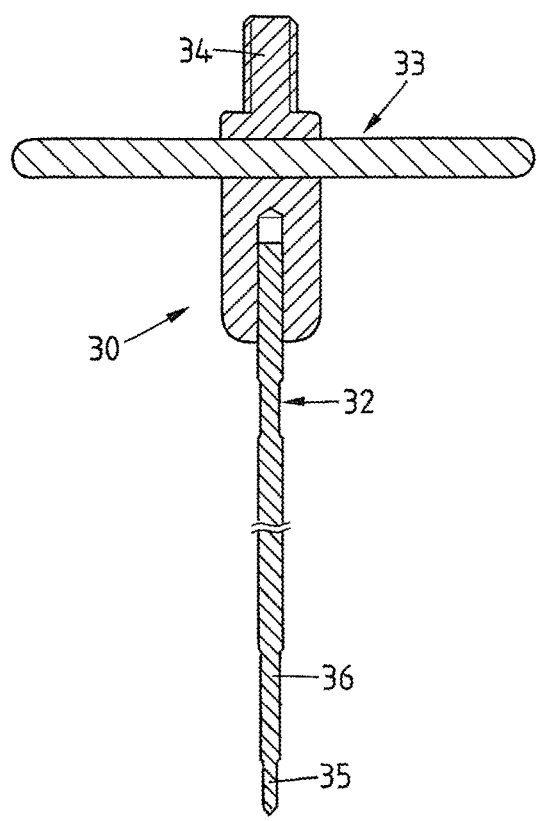
FIGS. 15 to 18 illustrate exemplary tools applicable for removing a fastener being implanted in a bone opening e.g. for fastening a soft tissue graft in this opening.
Figure 16:
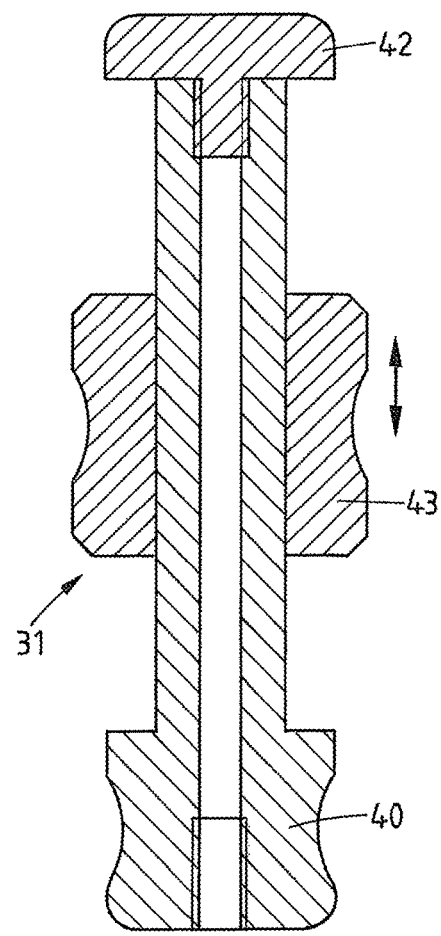

FIGS. 15 and 16 illustrate a removal tool 30 (FIG. 15) and a knock-out extension 31 (FIG. 16) which is attachable to the removal tool of FIG. 15. Removal tool and knock-out extension are applicable for removing a fastener which is, for example, press-fitted and anchored in a bone opening with the aid of the method as described in the preceding FIGS. 1 to 14, in particular such a fastener comprising a cavity that is open at the proximal fastener face and that is at least partly filled with the liquefiable material or such a fastener consisting of the liquefiable material.

The removal tool 30 comprises a removal rod 32, which is preferably slightly flexible (similar to a K-wire), and is attached to a handle portion 33, which is suitable for rotating the removal rod 32 around its own axis. The handle portion 33 comprises means for attachment of the knock-out extension 31, such as a threaded peg 34. The removal rod 32 comprises a distal end portion 35 equipped as a drill suitable, for example, for drilling a bore into the liquefiable material of the fastener, and adjacent to the drill portion 35 a screw portion 36 of a diameter larger than the diameter of the drill portion and being equipped as a self tapping screw.

For removal of the fastener, the proximal fastener face is made accessible. Then a bore is provided extending from the proximal fastener face with the aid of the drill portion 35, immediately followed by screwing the screw portion 36 into the bore. As soon as the screw portion 36 is held in the fastener sufficiently, the removal tool is pulled in a direction away from the proximal fastener face and therewith the fastener is removed from the bone opening.

If the pulling force necessary for removal of the fastener is high, the knock-out extension 31 may be attached to the handle portion 32 of the removal tool 30. For this purpose the knock-out extension 31 comprises, for example, a distal portion 40 equipped with an inner thread for being screwed onto the threaded peg 34 of the removal tool 30. The knock-out extension 31 further comprises a proximal stop element 42 and a hammer element 43, the hammer element being arranged between the distal portion 40 and the stop portion 42 in an axially moveable manner (double arrow). For knocking the fastener out of the bone opening, the knock-out extension 31 is attached to the proximal end of the removal tool 30 and then the hammer element 43 is knocked against the stop portion 42 effecting a hammering action on the fastener in a direction out of the bone opening.

Figures 17, 18:
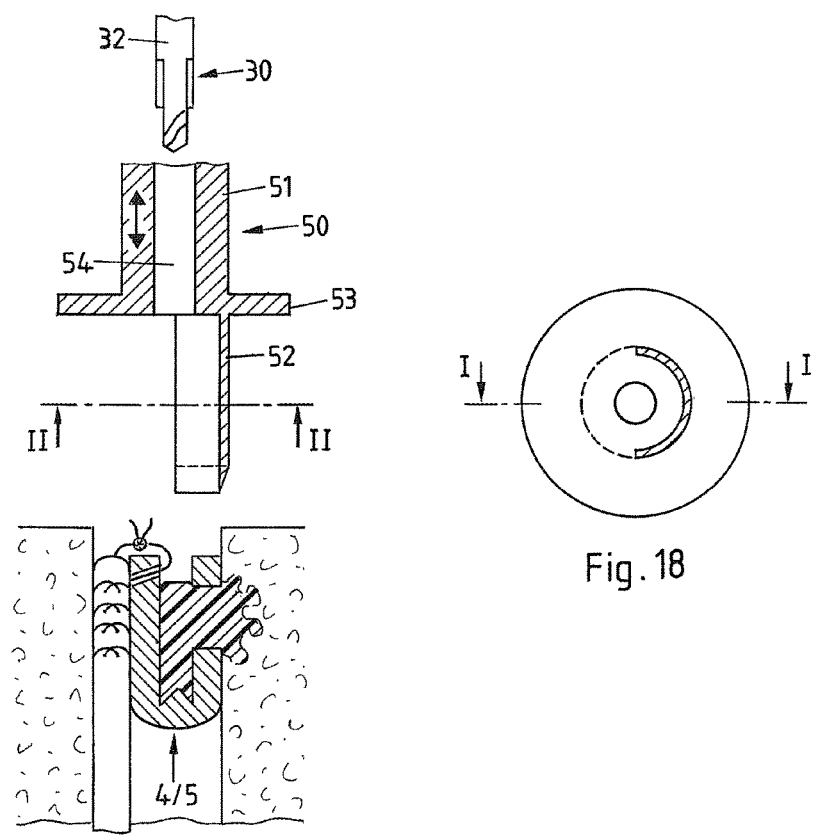

FIGS. 17 and 18 illustrate an exemplary punching tool 50 which is applicable in a method for removing an implanted element (e.g., a fastener 4/5 as described in connection with FIGS. 1 to 14), which is anchored in bone tissue with the aid of in situ liquefaction of a material having thermoplastic properties. Such removal of a fastener according to FIGS. 1 to 14 is carried out, for example, for a fastener comprising material that is not bio-degradable after a healing period in which the graft is connected to the wall of the bone opening by new bone growth such that retention by the fastener is not needed any more. The punching tool 50 is designed for cutting the positive-fit connection between the implanted element or fastener 4/5 and the bone tissue surrounding the latter and therewith loosening the fastener in the bone opening in which it is implanted. FIG. 17 is an axial section (section plane I-I in FIG. 18) of the punching tool 50 (only distal end shown) and the implanted fastener 4/5 and it also shows the distal end of a removal tool which may, for example, be the removal tool 30 according to FIG. 15 being used in cooperation with the punching tool 50. FIG. 18 is a cross section through the punching tool 50 (section plane II-II in FIG. 17).

The punching tool 50 substantially comprises a sonotrode 51 suitable for transmitting mechanical vibration, in particular ultrasonic vibration, from a proximal to a distal end thereof, wherein the proximal sonotrode end (not shown in FIG. 17) is designed for being coupled to a vibration source (ultrasonic transducer and possibly booster), and wherein the distal sonotrode end is equipped with a suitably sharp punching blade 52, which is adapted to a cross section of the fastener 4/5 to be removed such that on being forced and simultaneously vibrated it is capable to cut between the fastener and the bone tissue surrounding the latter at least where the fastener is anchored in the bone tissue, i.e. where the material having thermoplastic properties reaches into the bone tissue, thereby separating the fastener 4/5 from the bone tissue. Preferably the punching tool 50 comprises means such as a collar 53 that limits the depth to which the punching blade 52 can be forced into the bone tissue, wherein the collar 53 is arranged to abut the bone surface or possibly the proximal face of the fastener 4/5 when the depth limit is reached.

Furthermore, the punching tool 50 may comprise an axial channel 54 of a cross section adapted to the removal rod 32 of the removal tool 30 therewith being able to be guided to the fastener 4/5 by the removal rod 32.

The punching blade 52 of the punching tool 50 as shown in FIGS. 17 and 18 has a cross section in the form of a circular arch (e.g., semi-circular arch) and therefore is particularly suitable for cutting a one-sided anchorage of a substantially cylindrical fastener having a substantially circular cross section (anchorage not extending all around the fastener). For cutting an anchorage of a fastener of a different cross section, the punching blade of the punching tool is correspondingly shaped and extends either partly around such cross section or wholly, in the latter case being tube-shaped with a distal cutting edge which is closed in itself.

As mentioned above, the punching tool 50 is particularly suitable to be used in cooperation with a removal tool, for example, with the removal tool as illustrated in FIGS. 15 and 16, but may also be used either by itself or in cooperation with any other suitable removal tool. For removing the fastener 4/5 with the aid of cooperating punching and removal tool, the distal end of the removal rod 32 (which is, for example, a K-wire comprising a distal end suitable for drilling and attaching to the fastener with the aid of a screw thread) is first attached to the fastener. Then the punching tool 50 is positioned by sliding the punching tool 50 along the removal rod 32, the latter extending through the axial channel 54 of the punching tool 50. Then the punching blade 52 is forced between the fastener 4/5 and the bone tissue with the aid of mechanical vibration. When the punching blade 52 has reached the depth limit, i.e. when the collar 53 abuts against the bone surface or the proximal fastener face respectively, the removal tool 30 is pulled out of the punching tool 50 such removing the fastener 4/5 being attached to the distal end of the removal rod 32.

The punching tool 50 as illustrated in FIGS. 17 and 18 is similar to the punching tool as disclosed in the publication WO 2008/131884 whose content is enclosed herein in its entirety by reference.

What is claimed is:

1. A fastener for fastening an end portion of a soft tissue graft in an opening provided in a bone of a human or animal patient, said soft tissue graft end portion having at least one suture extending therefrom, the fastener comprising:
    a press-fit element, said press-fit element having a distal end and a proximal end, said distal end being inserted into the opening provided in the bone, said press-fit element having a wall that defines a cavity, said cavity extending from the proximal end toward the distal end of the press-fit element and being in communication with the opening in the bone;
    an anchoring element, said anchoring element being formed from an in-situ liquefiable material having thermoplastic properties and being inserted into the cavity from the proximal end of the press-fit element toward the distal end of the press-fit element;
    wherein the press-fit element defines a suture passage along which the suture extends and that permits tying said at least one suture to the fastener, wherein the suture passage has a mouth at the proximal end of the press-fit element and extends into the press-fit element wall from said suture passage mouth in spaced relation to the cavity.

2. The fastener according to claim 1, wherein the suture passage extends from the proximal end of the press-fit element to a circumferential surface of the press-fit element.

3. The fastener according claim 1, wherein the press-fit element cavity is open at a proximal face of the press-fit element and comprises a fenestration or perforation to a circumferential surface of the press-fit element, and wherein the anchoring element is adapted to be received in the cavity.

4. The fastener according to claim 3, wherein the cavity extends axially through the press-fit element.

5. The fastener according to claim 3, wherein the cavity extends at an angle to an axis of the press-fit element and has an open mouth, which constitutes the fenestration, on the circumferential surface of the press-fit element.

6. The fastener according to claim 1, wherein the suture passage includes at least one groove extending across a proximal face of the press-fit element.

7. The fastener according to claim 1, wherein the press-fit element has a circumferential surface and the cavity extending from the proximal end toward the distal end of the press-fit element is formed as at least one groove extending axially along said circumferential surface, and the anchoring element is adapted to be at least partially received within the said at least one groove.

8. The fastener according to claim 1, wherein the anchoring element is integrated in the press-fit element, by the press-fit element comprising a corresponding portion of the material having thermoplastic properties.

9. The fastener according to claim 1, said press-fit element further defining an axial channel for guidance along a K-wire, the axial channel extending centrally or ex-centrically through the fastener.

10. The fastener according to claim 1, wherein the suture passage extends from a proximal face of the press-fit element to the distal end of the press-fit element.

11. A fastener according to claim 1 for use in a method for fastening an end portion of a soft tissue graft in an opening provided in a human or animal bone.

* * * * *